United States Patent [19]

Kelman

[11] Patent Number: 4,608,049
[45] Date of Patent: Aug. 26, 1986

[54] INTRAOCULAR LENS AND METHOD OF INSERTING AN INTRAOCULAR LENS INTO AN EYE

[76] Inventor: Charles D. Kelman, 269-70 Grand Central Pkwy., Floral Park, N.Y. 11005

[21] Appl. No.: 393,057

[22] Filed: Jun. 28, 1982

[51] Int. Cl.⁴ .............................................. A61F 2/16
[52] U.S. Cl. ................................................... 623/6
[58] Field of Search ........................... 3/13, 1; 623/6

[56] References Cited

U.S. PATENT DOCUMENTS

| | | | |
|---|---|---|---|
| 3,711,870 | 1/1973 | Deitrick | 3/13 |
| 3,992,563 | 11/1976 | Tanaka | 3/13 X |
| 4,092,743 | 6/1978 | Kelman | 3/13 |
| 4,163,608 | 8/1979 | Neefe | 3/13 X |
| 4,172,297 | 10/1979 | Schlegel | 3/13 |
| 4,174,543 | 11/1979 | Kelman | 3/13 |
| 4,206,518 | 6/1980 | Jardon et al. | 3/13 |
| 4,253,199 | 3/1981 | Banko | 3/13 |
| 4,373,218 | 2/1983 | Schachar | 3/13 |
| 4,402,579 | 9/1983 | Poler | 3/13 X |
| 4,573,998 | 3/1986 | Mazzocco | 623/6 |

FOREIGN PATENT DOCUMENTS 2556665 6/1977 Fed. Rep. of Germany .......... 623/6

Primary Examiner—Ronald L. Frinks
Attorney, Agent, or Firm—Henry Sternberg; Bert J. Lewen

[57] ABSTRACT

An intraocular lens which may be inserted into the eye through a smaller incision in the cornea than another lens with an optic of the same diameter and is adapted to seat adjacent the periphery of the iris. The optic is deformable so that the optic may be in contracted condition while the lens is being inserted through the incision.

4 Claims, 10 Drawing Figures

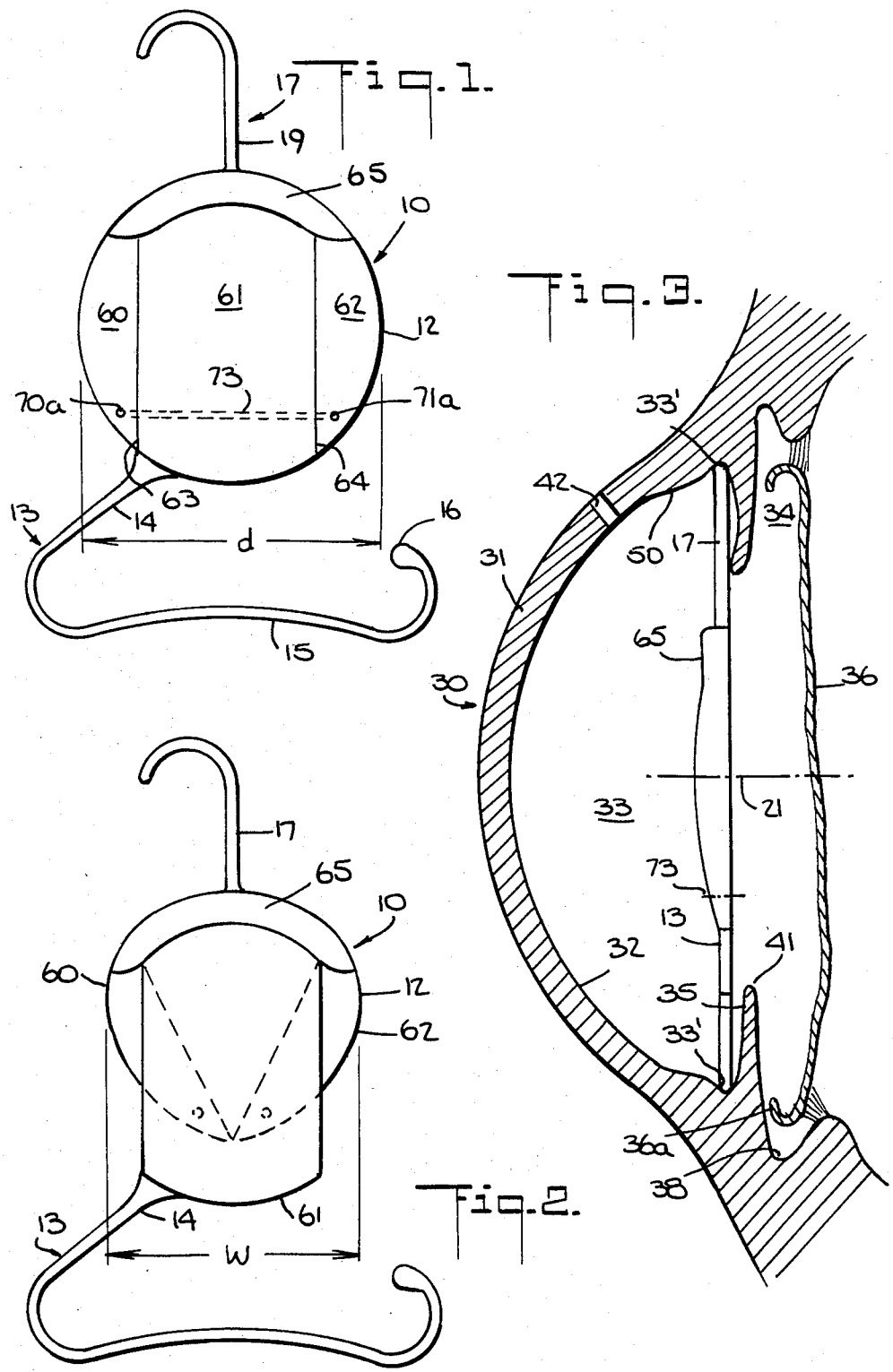

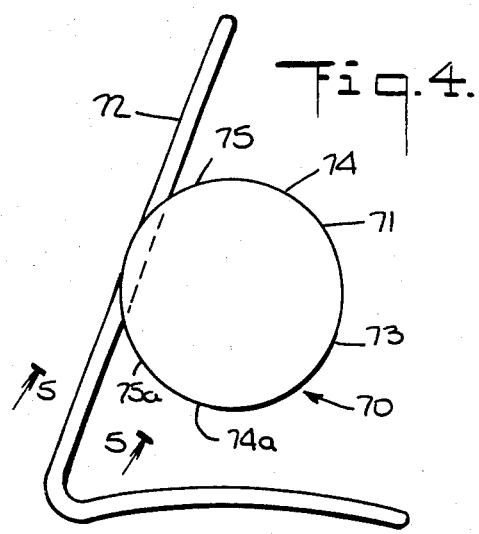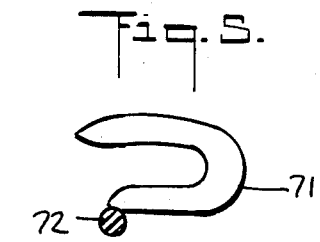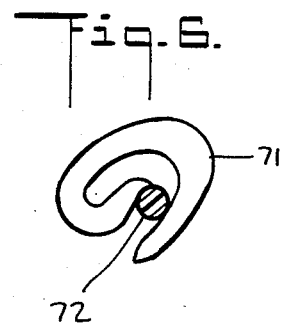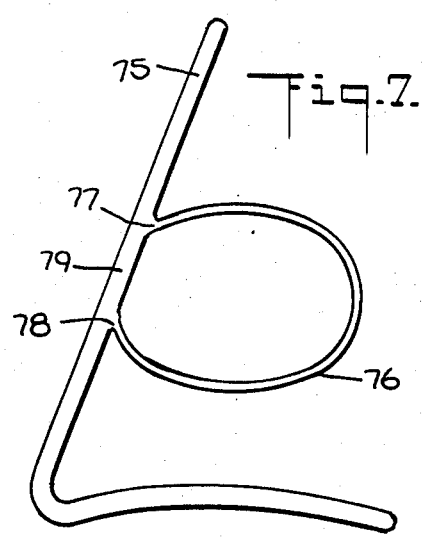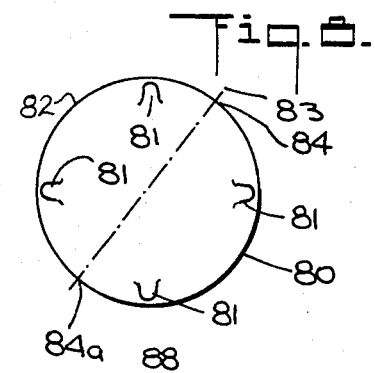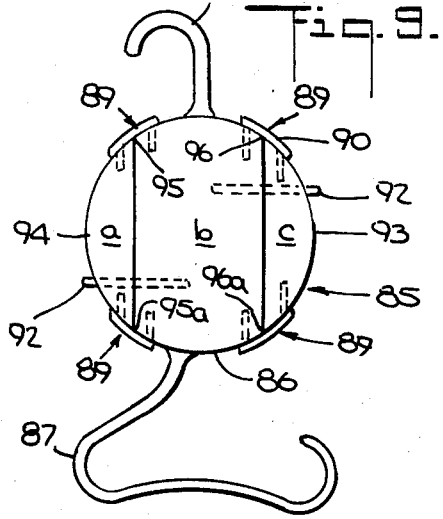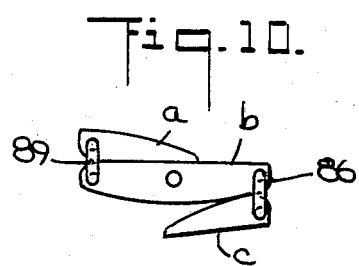

INTRAOCULAR LENS AND METHOD OF INSERTING AN INTRAOCULAR LENS INTO AN EYE

BACKGROUND OF THE INVENTION

The present invention relates to an intraocular lens which is adapted to be seated in the eye adjacent the periphery of the iris, for example, in the anterior chamber, the posterior chamber or partly in the anterior chamber and partly in the posterior chamber, after the removal of a natural lens. The invention also relates to a method of inserting an intraocular lens into an eye.

It has been found that the insertion of an intraocular lens is by far the best solution to correcting vision after cataract surgery. The proper implantation of an intraocular lens always involves the risk of damage to the eye particularly during the insertion process as well as at a later time if the intraocular lens dislocates or must be removed or replaced.

To place the lens in the eye adjacent the periphery of the iris, the surgeon ordinarily makes an incision or opening in the cornea which aligns with the pupil, and the surgeon passes the lens through the opening. In many of the more recent lenses the position-fixation members of the lens are either no wider than the lens body, or are flexible and can be bent to pass through an opening which is about the same size as the lens body or can be snaked through such opening. Accordingly, the minimum length of the opening which must be made is ordinarily determined by the diameter of the lens body, or optic, which ordinarily has a circular periphery and which is substantially rigid, being formed of a material such as, for example, methylmethacrylate and having a configuration which provides the desired optical characteristics. It is, of course, desirable to make the opening in the cornea as small as possible to minimize the risk of damage to the eye.

Other types of intraocular lenses are known which are flexible and which are secured to the iris. Such lenses can not be seated in the eye adjacent the periphery of the iris. One such lens described in U.S. Pat. No. 4,172,297 has a position-fixation flange surrounding the light-focusing lens body or optic for securing to the iris and thus the lens is not adapted for insertion through an incision smaller than the diameter of the lens body. Another such lens described in U.S. Pat. No. 4,206,518 has a pair of wide position-fixation members extending from opposite peripheral regions of the light-focusing lens body or optic for connection to the iris and this lens also is not adapted for insertion through an incision smaller than the diameter of the lens body. Still another such lens, described in U.S. Pat. No. 4,253,199, has a peripheral lip for suturing to the ciliary body of the eye for deforming the lens body in accordance with the expansion and contraction of the ciliary body so as to change the optical characteristics of the lens body in response thereto. The lens bodies of these prior lenses are impeded by the position-fixation members integral therewith from being adapted for insertion through an incision smaller than the diameter of the lens body.

SUMMARY OF THE INVENTION

It is an object of the present invention, therefore, to provide a new and improved intraocular lens and method of inserting such a lens into an eye which avoid one or more of the disadvantages of prior such lenses and methods of inserting such lenses into eyes.

It is another object of the invention to provide a new and improved intraocular lens which can be inserted into the eye through a smaller opening than was heretofore required for a lens with an optic of the same diameter.

It is another object of the invention to provide a new and improved lens body for an intraocular lens, which lens body can be inserted into the eye through a smaller opening than was heretofore required for a lens body of the same diameter.

It is another object of the invention to provide a new and improved method of inserting an intraocular lens into an eye through a smaller opening than was heretofore required for a lens with an optic of the same diameter.

It is another object of the invention to provide a new and improved method of inserting an intraocular lens body into the eye through a smaller opening than was heretofore required for a lens body of the same diameter.

In accordance with the invention, an intraocular lens comprises a deformable lens body which can be so deformed to a dimension smaller than the maximum dimension of the lens body when undeformed that the lens body can be inserted into the eye, when the lens body os deformed, through a smaller opening in the eye than the opening through which the lens body could be inserted when undeformed. The lens body is capable of return to substantially its undeformed configuration after insertion into the eye. The lens also includes position-fixation means extending from different peripheral regions of the lens body and adapted to seat within an eye adjacent the periphery of the iris for fixing the position of the lens body within the eye.

Also in accordance with the invention, an intraocular lens comprises a lens body and at least a pair of position-fixation members extending from different peripheral regions of the lens body and adapted to seat within an eye adjacent the periphery of the iris for fixing the position of the lens body within the eye. The lens body has a plurality of separate portions in an initial relation and a bridging portion of the lens body connecting the plurality of portions. The bridging portion is sufficiently flexible that the aforesaid plurality of portions can be overlapped upon the application of force thereto. The bridging portion is capable of returning the aforesaid plurality of portions substantially to their initial relation upon release of the force therefrom.

Also in accordance with the invention, an intraocular lens comprises a deformable lens body having at least one flexible portion and which can be so folded to a dimension smaller than the maximum dimension of the lens body when undeformed that the lens body can be inserted into the eye, when the lens body is deformed, through a smaller opening in the eye than the opening through which the lens body could be inserted when undeformed. The lens body is capable of return to substantially its undeformed configuration after insertion into the eye. The lens body has a free periphery along at least one peripheral region generally parallel to the direction of the fold and has peripheral regions adjacent opposite ends of the fold which are free of substantial impediment to folding the lens body along the fold.

Also in accordance with the invention, a lens body for an intraocular lens and adapted for insertion into the eye through an opening therein comprises a deformable lens body having at least one substantially rigid portion and which can be so deformed to a dimension smaller than the maximum dimension of the lens body when undeformed that the lens body can be inserted into the eye, when the lens body is deformed, through a smaller opening in the eye than the opening through which the lens body could be inserted when undeformed. The lens body is capable of return to substantially its undeformed configuration after insertion into the eye.

Also in accordance with the invention, a lens body for an intraocular lens and adapted for insertion into the eye through an opening therein comprises a plurality of separate portions held in an initial relation by a bridging portion of the lens body connecting the plurality of portions. The bridging portion is sufficiently flexible that the plurality of portions can be overlapped upon the application of force thereto and the bridging portion is capable of returning the plurality of portions substantially to their initial relation upon release of the force therefrom.

Also in accordance with the invention, a lens body for an intraocular lens and adapted for insertion into the eye through an opening therein comprises a deformable lens body having at least one flexible portion and which can be so folded to a dimension smaller than the maximum dimension of the lens body when undeformed that the lens body can be inserted into the eye, when the lens body is deformed, through a smaller opening in the eye than the opening through which the lens body could be inserted when undeformed. The lens body is capable of return to substantially its undeformed configuration after insertion into the eye. The lens body has a free periphery along at least one peripheral region generally parallel to the direction of the fold and has peripheral regions adjacent apposite ends of the fold which are free of substantial impediment to folding the lens body along the fold.

Also in accordance with the invention, a method of inserting into an eye an intraocular lens having a deformable lens body and position-fixation means adapted to seat within the eye adjacent the periphery of the iris for fixing the position of the lens body within the eye comprises so deforming the lens body to a dimension smaller than the maximum dimension of the lens body when undeformed that the lens body can be inserted into the eye, when the lens body is deformed, through a smaller opening in the eye than the opening through which the lens body could be inserted when undeformed. The method also includes inserting the deformed lens body into the eye through the opening which is smaller than the maximum dimension of the lens body when undeformed and inserting the position-fixation means into the eye through the aforesaid opening.

Also in accordance with the invention, a method of inserting into an eye a deformable intraocular lens body comprises so deforming the lens body to a dimension smaller than the maximum dimension of the lens body when undeformed that the lens body can be inserted into the eye, when the lens body is deformed, through a smaller opening in the eye than the opening through which the lens body could be inserted when undeformed. The method includes inserting the deformed lens body into the eye through the opening which is smaller than the maximum dimension of the lens body when undeformed.

For a better understanding of the present invention, together with other and further objects thereof, reference is made to the following description taken in connection with the accompanying drawings, and its scope will be pointed out in the appended claims.

BRIEF DESCRIPTION OF THE DRAWINGS

FIG. 1 is a plan view of an embodiment of the present invention intended for fixation in, for example, the anterior chamber of the eye.

FIG. 2 is a plan view of the FIG. 1 lens subjected to compressive force prior to insertion in the eye.

FIG. 3 is a side elevational view of the FIG. 1 lens fixed within an eye, shown in section.

FIG. 4 is a plan view of another embodiment of the lens of the present invention intended for fixation in, for example, the anterior chamber of the eye.

FIG. 5 is a side elevational view of the lens body of FIG. 4, taken along line 5—5 of FIG. 4, but with the lens body in a deformed condition.

FIG. 6 is a side elevational view of the lens body of FIG. 4, represented in another deformed condition.

FIG. 7 is a plan view of a portion of another embodiment of the lens of the present invention intended for fixation in, for example, the anterior chamber of the eye.

FIG. 8 is a plan view of a lens body adapted for attachment to the FIG. 7 lens portion;

FIG. 9 is a plan view of another embodiment of the lens of the present invention intended for fixation in, for example, the anterior chamber of the eye.

FIG. 10 is a side elevational view of the lens body of FIG. 9 in a folded condition.

DESCRIPTION OF THE PREFERRED EMBODIMENTS

With reference to the drawings, the invention as a whole is depicted in the figures and denoted by reference character 10. The intraocular lens structure 10 includes as one of its elements a medial, light-focusing lens body or optical zone 12, FIG. 1. The lens body 12 may be constructed of any biologically inert, transparent material suitable for optical correction such as methylmethacrylate and other materials known in the art.

Lens structure 10 is intended for insertion and fixation within an eye 30, after cataract removal. Eye 30 includes a cornea 31 having an endothelial layer 32. Anterior chamber 33 and posterior chamber 34 are defined by the position of iris 35. FIG. 3 shows eye 30 after an extra capsular surgical procedure in which, after the natural lens has been removed, a posterior capsule membrane 36, as well as a small part of anterior capsule 36a remains. Ciliary sulcus 38 of the posterior chamber is located between the sulcus of the capsule 36 and the iris 35. As used in this specification and in the claims, the term "adjacent the periphery of the iris", referring to seating, includes seating in the anterior chamber angle of the eye in the vicinity of the scleral spur 50, seating in the sulcus of the capsule 36, 36a, and seating in the ciliary sulcus 38.

At least a pair of position fixation members 13, 17 are connected with the lens body 12 and extend from different peripheral regions of the lens body and are adapted to seat within an eye for fixing the position of the lens body within the eye. First position fixation member 13 has a first portion 14 contiguous to and extending generally laterally outwardly from a first region of the periphery of the lens body 12. First position fixation member 13 has a second portion 15 extending from the end of the first portion 14 generally transversely thereto and at least partly peripherally of the lens body 12 to provide two points of support for the lens in, for example, the anterior chamber of the eye. A knob 16 is fixed to the terminal end of portion 15 to prevent damage to human tissue within the eye.

As seen in FIG. 1 lens structure 10 includes a second position fixation member 17 as a necessary element thereof. Second member 17 includes a first portion 19 extending generally laterally outwardly from a second region of the periphery of the lens body 12 spaced from the first region and in a direction generally opposite to that of the first position fixation member 13 for extending to the periphery of the iris for seating in, for example, the anterior chamber angle 33' of the eye in the vicinity of the scleral spur 50, as represented in FIG. 3.

First and second position fixation members 13, 17 may be molded integrally with lens body 12 or connected thereto by an adhesive, ultrasonic welding, fusion, or any other connection method known in the art. It should be noted that first and second position fixation members 13, 17 are constructed of biologically inert and nonabsorbative material such as methylmethacrylate, and the like. In the present embodiment first and second members 13, 17 are resilient or apringy such that they will return toward the position shown in FIG. 1 after compression or extension away from the represented configuration.

According to one embodiment of the invention the lens body has at least one substantially rigid portion 61 and preferably has a circular periphery and has a plurality of separate portions, for example, three substantially rigid portions 60, 61, 62, in an initial relation preferably separated by a pair of cuts 63, 64, extending longitudinally across the lens body 12 to a bridging portion 65 of the lens body 12 connecting the plurality of portions 60, 61, 62. The small portions of the bridging portion 65, at the ends of the cuts 63, 64 are flexible so that the plurality of portions 60, 61, 62 may be overlapped upon the application of force thereto, as represented in FIG. 2. The bridging portion 65 is capable of returning the plurality of portions 60, 61, 62 substantially to their initial relation upon release of the force therefrom. The bridging portion 65 preferably is an outer edge of the lens body and may be thicker than the edge of the lens body over the major portion of the lens body to provide resilient strength.

Each of the two outer portions 60, 62 of the lens body may have an aperture 70a, 71a therein adapted to receive a suture 73, represented in broken line construction in FIG. 1, for maintaining the three lens body portions 60, 61, 62 in a desired fixed relation to one another, which preferably is substantially their initial relation as represented in FIG. 1, when the lens is seated in the eye.

Alternatively to utilizing apertures 70a, 71a and suture 73, each of the two outer portions 60, 62 may have a small lateral projection thereon (not shown) which projects across the cut 63 or 64 in the vicinity of where suture 73 is indicated into a corresponding lateral aperture in portion 61 for maintaining the three lens body portions 60, 61, 62 in substantially their initial relation, as represented in FIG. 1, when the lens is seated in the eye.

In order to place the lens in the eye through an incision 42 made by the surgeon in the cornea 31 above the end of the endothelial layer 32 which aligns with pupil 41, the surgeon deforms the lens body as represented in FIG. 2. The width w of the lens body deformed as represented in FIG. 2 is much smaller than the diameter d of the lens body when undeformed as represented in FIG. 1. The position fixation members 13, 17 are shaped such that they can be snaked through the incision 42. The maximum transverse dimension corresponding to the width w of the deformed lens body 60, 61, 62 is represented in FIG. 2. The incision 42, therefore, needs to be only sufficiently long that the width w of the deformed lens body 60, 61, 62 represented in FIG. 2 can pass through the incision 42. A pair of tweezers may be employed to stabilize and to steer the lens body 60, 61, 62 and first member 13 into seating engagement in the anterior chamber angle 33'. Second member 17 is then seated in the anterior chamber angle 33' for fixating the lens 10 in the anterior chamber.

After the lens is seated in the eye, a suture 73 may be passed through apertures 70a, 71a as represented in FIG. 1 to maintain the lens body portions 60, 61, 62 in substantially their initial flat relation as represented in FIGS. 1 and 3.

From the foregoing description, it will be seen that an intraocular lens 10 in accordance with the invention comprises a deformable lens body 12 which can be so deformed to a dimension w, as represented in FIG. 2, which is smaller than the maximum dimension d of the lens body 12 when undeformed, as represented in FIG. 1, that the lens body 12 can be inserted into the eye, when the lens body 12 is deformed, through a smaller opening in the eye than the opening through which the lens body 12 could be inserted when undeformed. The lens body 12 is capable of return to substantially its undeformed configuration after insertion into the eye.

Referring now to FIG. 4 of the drawings, an intraocular lens 70 comprises a deformable lens body 71 which can be so deformed to a dimension which is smaller than the maximum dimension of the lens body 70 when undeformed, as represented to FIG. 4, that the lens body 71 can be inserted into the eye, when the lens body 71 is deformed, through a smaller opening in the eye than the opening through which the lens body 71 could be inserted when undeformed. The lens body 71 is capable of return to substantially its undeformed configuration after insertion into the eye.

The lens body 71 preferably has a circular periphery with a diameter of, for example, 6 mm. The lens body 71 may, for example, be made of silicone rubber or an acrylate polymer (such as a terpolymer of 2-hydroxyethylmethacrylate, N-vinyl-2-pyrrolidone, and methacrylic acid, with ethyleneglycol dimethacrylate as a crosslinking agent) and, therefore, has a pliable, rubbery consistency. The silicone rubber material may, for example, by a hydroxydimethylsilane which is optically clear, stable with good mechanical strength and highly elastic. Such material is commercially available in Silarx, a registered trademark, (dimefocon A) contact lenses manufactured by Danker Laboratories, Inc. The lend body 71 may be molded, glued or otherwise attached to a position-fixation member 72, preferably along a chord of the lens body 71. The position-fixation member 72 is of similar material to the FIG. 1 position-fixation members 13, 17 and is adapted to provide similar three-point fixation of the lens within the eye.

To insert the lens 70 into the eye through an opening in the cornea, the lens body 71 may be folded over as represented in FIG. 5 or folded in a curl as represented in FIG. 6 to a width of, for example, 3 mm or less. Since the position-fixation member 72 can be snaked through an opening in the eye of less than 2 mm, the curled dimension of the lens body will control the minimum size of incision required. Accordingly, an incision of ony about 3 mm would be required. The lens body 71 is capable of return to substantially its undeformed configuration after insertion into the wyw. It should be noted that the drawings, particularly FIGS. 5 and 6, show the thickness of the folded lens body exaggerated for purposes of illustration. The lens body may be held in this folded condition by the instrument used by the surgeon for inserting the lens body through the incision, or a means such as a suture placed around the folded lens body may be used to maintain the lens body in folded condition during insertion. Such suture can be cut and removed once the lens body is within the eye.

The lens body 70 has a free periphery along at least one region 73 generally parallel to the direction of the fold of the lens body 70 and has peripheral regions 74, 75 and 74a, 75a adjacent the opposite ends of the folds represented in FIGS. 5 and 6 which are free of substantial impediment to folding the lens body along the folds.

Referring now to FIG. 7, there is represented a positionfixation member 75 similar to the position-fixation member 72 but with a flexible loop 76 comprising, for example, a strand of plastic material such as Supramid, attached at two points of the member 72 which are preferably positioned on both sides of the center of the leg portion 79. The loop 76 preferably is generally elliptically shaped, with its major axis extending transverse to the leg portion 79. The flexibility of the loop 76 is such that it may be collapsed and inserted into the eye along with the leg portion 79 as the latter is inserted through the opening in the eye. The loop 76 is adapted to be connected inside the eye to a deformable lens body, for example as represented in FIG. 8, which is separately inserted into the eye.

The lens body 80 of FIG. 8 can be so deformed, for example, in a manner similar to those represented in FIGS. 5 and 6 for the lens body 71, to a dimension smaller than the maximum dimension of the lens body 80 when undeformed that the lens body 80 can be inserted into the eye, when the lens body is deformed, through a smaller opening in the eye than the opening through which the lens body could be inserted when undeformed. The lens body 80 is capable of return to substantially its undeformed configuration after insertion into the eye. To this end, the lens body 80 is of material similar to the lens body 71 of FIG. 4, for example silicone rubber, so that it is pliable and bendable for passing through a small incision. The lens body 80 preferably has a circular periphery and is adapted for attachment inside the eye to the strand 76 of FIG. 7 by, for example, short prongs or hooks 81 extending from one face of the lens body near the periphery thereof. These prongs or hooks may be molded as part of the lens body or may be, for example, hook shaped inserts of platinum or the like. The prongs or books 81 preferably are disposed at the corners of an imaginary rectangle of greater length than height so that the hooks 81 will fit inside the elliptical loop 76 and the lens body 80 may be twisted relative to the loop 76 to force the hooks 81 into gripping engagement with the loop 76. It will be understood that one instrument may be inserted by the surgeon through the incision 42 in the eye (FIG. 2) while a second instrument may be inserted by the surgeon through a second very small incision which is ordinarily made in the eye for other purposes. Using two instruments at the same time the surgeon can attach the lens body 80 to the loop 76 inside the eye as described.

The lens body 80 has a free periphery along at least one region 82 generally parallel to the direction of the fold, represented by broken line 83 in FIG. 8, of the lens body 80 and has peripheral regions 84 84a adjacent opposite ends of the fold which are free of substantial impediment to folding the lens body along the fold Referring now to FIG. 9 of the drawings, the lens 85 there represented may, for example, have a substantially rigid lens body 86 of a material similar to the FIG. 1 lens body and may have position-fixation members 87, 88 similar to the corresponding members of the FIG. 1 embodiment. The lens body 86, however, has three separate portions a, b, c which are pivotably connected together by, for example, suitable hinges 89, each of which may, for example, comprise a plate 90 through which a pin 91 rotatably extends at one end and is attached to a lens body portion at the other end.

As represented in FIG. 10, the end portion a may be folded over the central portion b and the end portion c may be folded under the central portion b. Accordingly, the position-fixation members 87, 88 can be snaked through the opening in the eye and the folded lens body 86 can be inserted into the eye through a smaller opening than the lens body 86 could be inserted when unfolded. After the lens is positioned inside the eye, the portions a, b, c of the lens body 86 can be unfolded to the condition represented in FIG. 9. Suitable lock pins 92 represented in broken-line construction in FIG. 9 can then be inserted into the lens body portions a, b, c to maintain them in fixed relationship. The surgeon may also use two instruments at the same time to unfold the lens body 86.

The lens body 86 has a free periphery along regions 93, 94 generally parallel to the directions of the folds and has peripheral regions 95, 95a and 96, 96a adjacent opposite ends of the folds which are free of substantial impediment to folding the lens body along the folds.

From the foregoing description it will be apparent that a lens constructed in accordance with the invention can be inserted into an eye through a smaller incision that the diameter of the undeformed lens body, thereby minimizing the risk of damage to the eye.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. An intraocular lens comprising:
   position-fixation means having an elongated intermediate portion having seating portions at opposite axial ends thereof for seating the lens within an eye,
   a deformable lens body of flexible material connected at a peripheral portion thereof to said position-fixation means, with the axis of said position-fixation means generally tangential to said peripheral portion, said lens body having light-focusing capability and adapted to be curled about said axis of said position-fixation means into a substantially cylindrical shape having a diameter substantially smaller than the maximum dimension of said lens body when uncurled, so that said lens can be inserted into the eye in the direction of said axis, when said lens body is in curled condition, through a substantially smaller opening in the eye than the opening through which said lens body could be inserted when uncurled, said lens body being formed of a material more flexible than the material of said intermediate portions of said position-fixation means and being capable of returning to substantially its uncurled configuration after insertion into the eye.

2. A lens in accordance with claim 1 in which said material is silicone rubber.

3. A lens in accordance with claim 1 in which said lens body is of circular shape and in which said position fixation means extends generally tangentially from given regions of said lens body and the remaining regions of the periphery of said lens body are free.

4. A method of inserting into an eye an intraocular lens having a deformable lens body of flexible material capable of focusing light rays and elongated position-fixation means connected to the lens body and adapted to seat within the eye adjacent the periphery of the iris for fixing the position of the lens body within the eye comprising:

curling said lens body about said elongated position-fixation means into substantially cylindrical shape, said cylindrical shape having an axis substantially parallel to the axis of said position-fixation means and a diameter smaller than the maximum dimension of said lens body when uncurled so that said lens can be inserted into the eye in the direction of said axis, when said lens body is in curled condition, through a smaller opening in the eye than the lens body could be inserted when uncurled;

inserting said lens with said lens body in curled condition, into the eye, in the direction of said axis, through said opening which is smaller than the maximum dimension of said lens body when uncurled; and seating said position-fixation means in the eye and permitting said lens body to uncurl within the eye to assume its original shape.

* * * * *